United States Patent [19]

Gillies et al.

[11] Patent Number: 4,910,590

[45] Date of Patent: Mar. 20, 1990

[54] ENDOSCOPE INSERTION DIRECTION DETECTION METHOD

[75] Inventors: Duncan F. Gillies; Gul N. Khan, both of London, England

[73] Assignee: Olympus Optical Co., Ltd., Tokyo, Japan

[21] Appl. No.: 291,772

[22] Filed: Dec. 29, 1988

[30] Foreign Application Priority Data

Nov. 16, 1988 [GB] United Kingdom ............... 88 26831

[51] Int. Cl.⁴ .......................... A61B 1/04; A61B 1/06
[52] U.S. Cl. ........................................ 358/98; 128/6; 364/413.13; 364/413.15; 364/413.22; 382/6
[58] Field of Search ................... 358/98; 128/6; 382/6; 364/413.13, 413.15, 413.22

[56] References Cited

U.S. PATENT DOCUMENTS 4,834,070 5/1989 Saitou .................................... 358/98

OTHER PUBLICATIONS

"A Highly Parallel Shaded Image Segmentation Method", Khan et al., International Conference on Parallel Architectures for Computer Vision and Display, Jan. 1988, Leeds University.

*Primary Examiner*—Howard W. Britton
*Attorney, Agent, or Firm*—Armstrong, Nikaido, Marmelstein, Kubovcik & Murray

[57] ABSTRACT

This endoscope insertion direction detection method comprises the steps of forming from the same endoscope image a plurality of picture images different in the number of pixels (or picture elements) and extracting a dark region in the picture image of a predetermined number of pixels by inspecting in the order of the picture images of less pixels the gray levels of the respective pixels in the plurality of picture images formed by the above mentioned forming step, the above mentioned dark region extracted by the above mentioned extracting step being considered to be the endoscope insertion direction. Preferably, the forming step includes gradually forming picture images of less pixels while reducing the number of pixels to ¼ so that, in the case where the number of pixels is reduced to ¼, the gray level of one pixel in the picture image of less pixels wil be of an average value of the gray levels of the four son pixels in the 2×2 square region in the picture image of more pixels corresponding to this one pixel.

14 Claims, 15 Drawing Sheets

FIG. 15
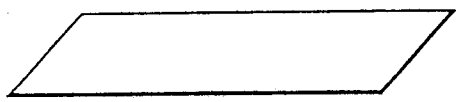
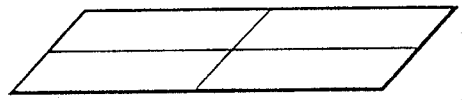
2 x 2
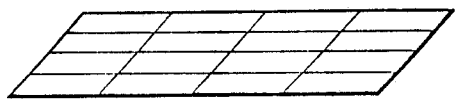
4 x 4
8 x 8
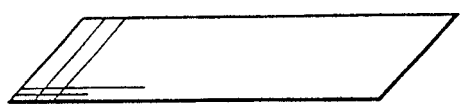
16 x 16
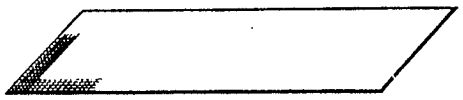
512 x 512

FLOOR P

FLOOR q

FLOOR r

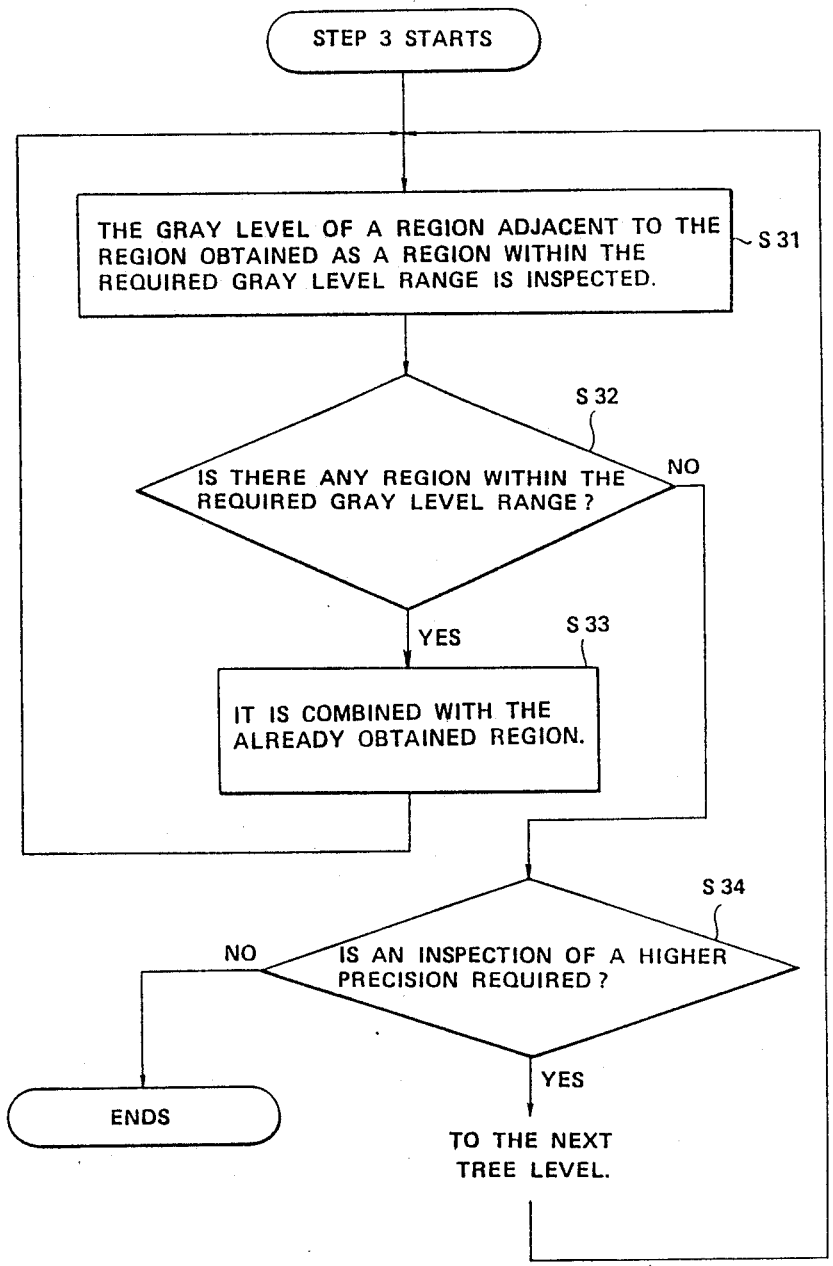

ENDOSCOPE INSERTION DIRECTION DETECTION METHOD

BACKGROUND OF THE INVENTION

1. Field of the Invention

This invention relates to methods of detecting the direction of insertion of an endoscope and more particularly to an endoscope insertion direction detecting method adapted to automatically inserting an endoscope in the large intestine inspection field.

2. Related Art Statement

Recently, there has been an extensive use of an endoscope whereby organs within a body cavity can be observed by inserting an elongated insertable part. Various curing treatments can be made by using treating tools inserted through a treating tool channel as required.

Now, in the conventional endoscope inspection, the doctor judges the advancing direction of the endoscope (insertable part) by observing the endoscope image while inserting the endoscope.

However, a high technique and skill are required to insert an endoscope in inspecting the large intestine.

OBJECT AND SUMMARY OF THE INVENTION:

An object of the present invention is to provide an endoscope insertion direction detection method whereby the endoscope insertion direction can be detected automatically during the treatment.

The endoscope insertion direction detection method of the present invention comprises the steps of forming from the same endoscope image a plurality of picture images different in the number of pixels (or picture elements) and extracting a dark region in the picture image of a predetermined number of pixels by inspecting in the order of the picture images of less pixels the mean gray levels of the respective pixels. The above mentioned dark region extracted by the above mentioned extracting step is considered to be the endoscope inserting direction. The above mentioned forming step involves forming picture images of less pixels each time reducing the number of pixels to ¼ so that, in the case where the number of pixels is reduced to ¼, the gray level of one pixel in the picture image of less pixels is an average of the gray levels of the four "son" pixels which form a 2×2 square in the picture image of more pixels.

The other features and advantages of the present invention will bocome apparent with the following explanation.

BRIEF DESCRIPTION OF THE DRAWINGS

FIGS. 7 to 18 relate to an embodiment of the present invention.

FIG. 7 is an explanatory view showing an example of an endoscope apparatus using a fiber scope and externally fitted television camera.

FIG. 8 is an explanatory view showing an example of an endoscope apparatus using a video scope.

FIG. 9 is a flow chart showing step 1 of this method.

FIG. 11 is an explanatory view showing node relations of the respective floors of the quad-tree.

FIG. 14 is a flow chart showing step 2 of this method.

FIG. 15 is an explanatory view showing a quad-tree for explaining step S22 of the step 2.

FIG. 18 is a flow chart showing step 3 of this method.

DETAILED DESCRIPTION OF PREFERRED EMBODIMENTS:

First of all, the summary of the present invention shall be explained with reference to FIGS. 1 to 6.

Figure 1:
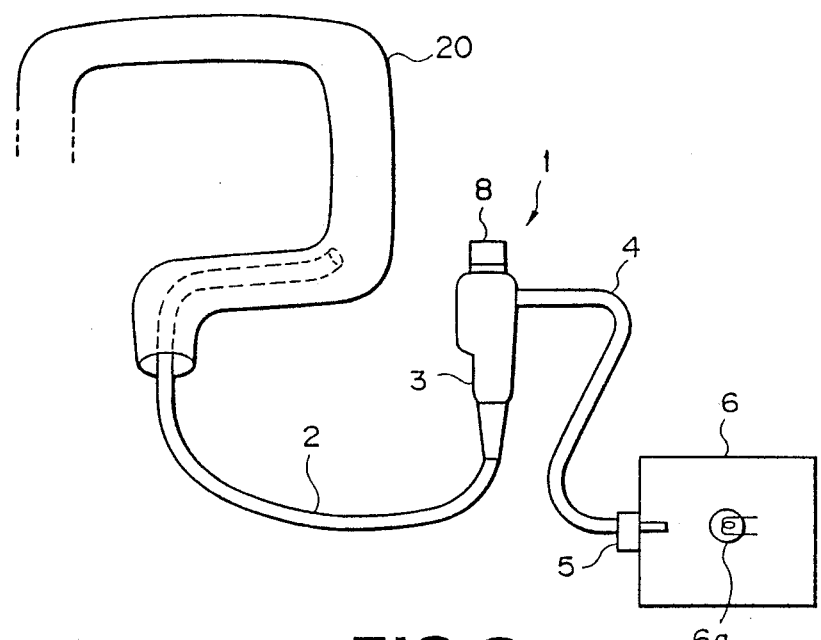
FIG. 1 is an explanatory view showing an endoscope inserted in the large intestine.

As shown in FIG. 1, an endoscope (fiber scope) 1 is provided with an elongated flexible insertable part 2 and a thick operating part 3 connected to the rear end of this insertable part 2. A flexible universal cord 4 is extended sidewise from the above mentioned operating part 3 and is provided at the tip with a connector 5 which is to be connected to a light source apparatus 6. The above mentioned operating part is provided at the rear end with an eyepiece part 8.

Figure 2:
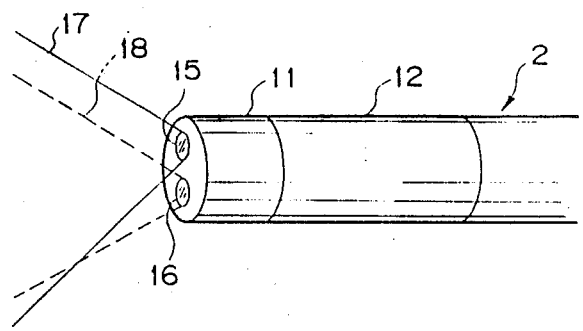
FIG. 2 is a perspective view showing a tip of an endoscope insertable part.

As shown in FIG. 2, a rigid tip part 11 and a rearward curvable part 12 adjacent to this tip part 11 are provided in turn on the tip side of the above mentioned insertable part 2. Also, the above mentioned operating part 3 is provided with a curving operation knob not illustrated so that the above mentioned curvable part 12 may be curved vertically and horizontally by rotating this curving operation knob.

An illuminating lens 15 of an illuminating optical system and an objective lens 16 of an observing optical system are arranged as directed substantially in the same direction in the above mentioned tip part 11. A light guide not illustrated made, for example, of a fiber bundle is provided on the rear end side of the above mentioned illuminating lens 15. This light guide is inserted through the above mentioned insertable part 2, operating part 3 and universal cord 4 and is connected to the above mentioned connector 5 so that, when this connector 5 is connected to the above mentioned light source apparatus 6, an illuminating light emitted out of a lamp 6a within this light source apparatus 6 will enter the entrance end of the above mentioned light guide, will be led to the tip part 11 by the above mentioned light guide, will be emitted out of the tip surface and will be radiated to an object through the above mentioned illuminating lens 15. By the way, in FIG. 2, the reference numeral 17 represents an illuminating range of the illuminating light.

On the other hand, the tip surface of the image, not illustrated, made of a fiber bundle is arranged in the image forming position of the above mentioned objective lens 16. This image guide is inserted through the above mentioned insertable part 2 and is extended to the above mentioned eyepiece part 8. The object image formed by the above mentioned objective lens 16 will be led to the above mentioned eyepiece part 8 and will be observed through an eyepiece lens, not illustrated, which is mounted in the eyepiece part 8. By the way, in FIG. 2, the reference numeral 18 represents a visual field range of the observing optical system.

Now, as shown in FIG. 2, the illuminating optical system and observing optical system of the endoscope 1 are adjacent to each other and are directed substantially in the same direction. In the case where there is no other illumination, the dark part of an endoscope image will be the farthest from the tip. Therefore, as shown in FIG. 1, in the case where the endoscope 1 (insertable part 2) is to be inserted into a closed tubular thing such as the large intestine 20, the endoscope 1 may be inserted in the direction of the darkest region of the obtained endoscope image. This shall be explained with reference to FIGS. 3 to 6. By the way, FIGS. 4 and 6 show parts of equal brightness by means of shading. The regions represented by the reference numerals 21, 22 and 23 show parts in increasing order of brightness.

Figure 3:
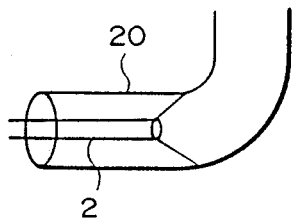
FIG. 3 is an explanatory view showing an endoscope inserted in a bent part of the large intestine.
Figure 4:
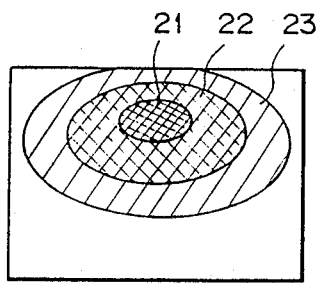
FIG. 4 is an explanatory view showing an endoscope image which would be seen with the endoscope as shown in FIG. 3.

FIG. 3 shows the insertable part 2 of the endoscope 1 inserted in the large intestine 20 where there is an upward bend. In such case, as shown in FIG. 4, the dark part in the endoscope image will appear at the top of the image. Therefore, in this case, the tip part 11 of the endoscope 1 may be curved upward and the insertable part 2 may be inserted upward.

Figure 5:
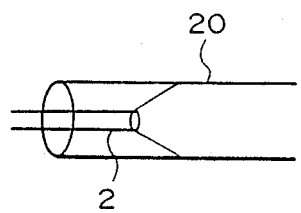
FIG. 5 is an explanatory view showing an endoscope as inserted in a straight part of the large intestine.
Figure 6:
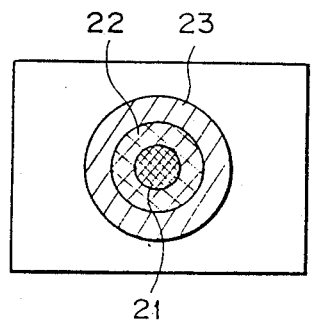
FIG. 6 is an explanatory view showing an endoscope image which would be seen with the endoscope as shown in FIG. 5.

FIG. 5 shows the insertable part 2 of the endoscope 1 inserted in a straight part of the large intestine 20. In such a case, as shown in FIG. 6, the dark part in the endoscope image will appear in the center. Therefore, in this case, the insertable part 2 of the endoscope 1 may be inserted straight as it is.

Thus, the endoscope inserting direction detecting method of the present invention is to detect the endoscope inserting direction by extracting the dark region of the endoscope image and is further to accurately extract the dark region of the endoscope image.

An embodiment of the present invention shall be explained in the following with reference to FIGS. 7 to 20.

Figure 7:
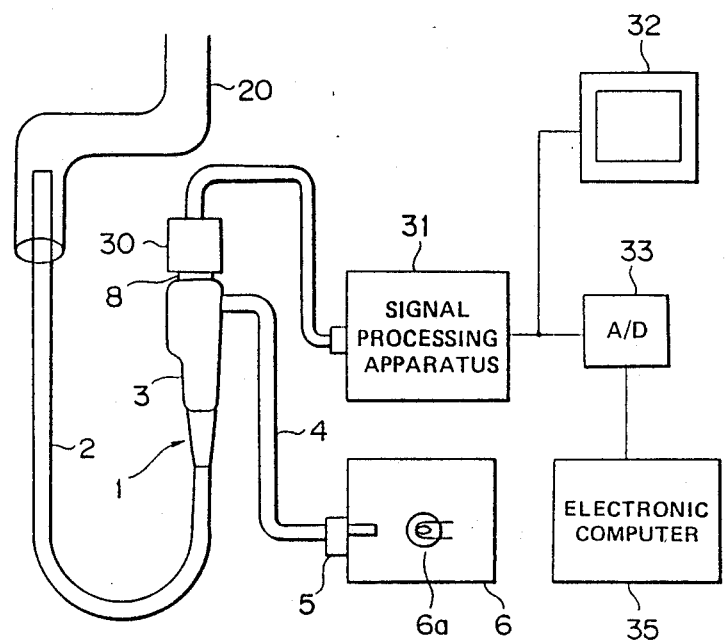
Figure 8:
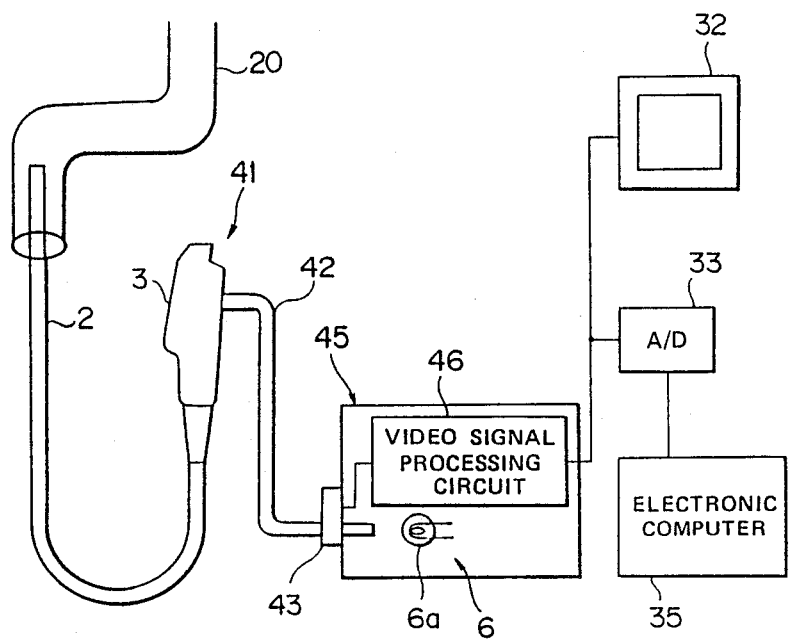

The endoscope insertion direction detection method of this embodiment is applied to an endoscope apparatus shown, for example, in FIG. 7 or 8.

The endoscope apparatus shown in FIG. 7 is provided with a fiber scope 1 fed with an illuminating light by a light source apparatus 6 and an externally fitted television camera 30 fitted to an eyepiece part 8 of this fiber scope 1. The formation of the above mentioned fiber scope 1 is the same as is shown in FIG. 1 and shall not be explained here. The above mentioned externally fitted television camera 30 is provided, for example, with an image forming lens not illustrated forming an image of a light from the above mentioned eyepiece part 8 and a solid state imaging device not illustrated arranged in the image forming position of this image forming lens. This externally fitted television camera 30 drives the above mentioned solid state imaging device and is to be connected to a signal processing apparatus processing the output signal of this solid state imaging device which is a video signal. The video signal output out of the above mentioned signal processing apparatus 31 will be input into a monitor 32, will be converted to a digital form by an A/D converter 33, will be then input into an electronic computer 35 and will be taken into a memory not illustrated within this electronic computer 35. The endoscope image will be displayed in the above mentioned monitor 32 and the endoscope inserting direction detecting method in this embodiment will be carried out by the above mentioned electronic computer 35.

The endoscope apparatus shown in FIG. 8 is provided with a video scope 41 instead of the fiber scope 1 and externally fitted television camera 30. The same as in the above mentioned fiber scope 1, this video scope 41 is provided with an elongated flexible insertable part 2 and an operating part 3 connected to the rear end of this insertable part 2. A flexible universal cord 42 is extended sidewise from the above mentioned operating part 3 and is provided at the tip with a connector 43 which is to be connected to a control apparatus 45 containing a light source apparatus 6 and video signal processing circuit 46. A solid state imaging device not illustrated is arranged in the image forming position of the objective lens in the tip part of the insertable part 2 of the above mentioned video scope 41 and is connected to a video signal processing circuit 46 within the above mentioned control apparatus 45 through the signal lines inserted through the above mentioned insertable part 2, operating part 3 and universal cord 42 and the above mentioned connector 43. By the way, the illuminating optical system of the above mentioned video scope 41 is the same as of the fiber scope 1 in that the illuminating light emitted from the lamp 6a of the light source apparatus 6 within the above mentioned control apparatus 45 may enter the entrance end of the light guide. The above mentioned solid state imaging device will be driven by the above mentioned video signal processing circuit 46 and the output signal of this solid state imaging device will be processed to be a video signal by the above mentioned video signal processing circuit. The same as in the endoscope apparatus using the fiber scope 1, the video signal output from this video signal processing circuit 46 will be input into the monitor 32, will be converted to be of a digital amount by the A/D converter 33, will be then input into the electronic computer 35 and will be taken into the memory not illustrated within this electronic computer 35. The endoscope image will be displayed in the above mentioned monitor 32 and the endoscope inserting direction detecting method in this embodiment will be carried out by the above mentioned electronic computer 35.

The endoscope inserting direction detecting method in this embodiment shall be explained in the following paragraphs.

By the way, it is usually the case that the number of pixels in a digital form of the image is $512 \times 512$ pixels and the brightness gradations are about 256 gradations. However, in the following explanation, in order to simplify the description, the number of pixels in the original picture taken into the electronic computer 35 shall be 8×8 and the gray levels shall be 8 gradations of 0 black gradation and 7 white gradations.

The endoscope insertion direction detection method in this embodiment comprises a step 1 of forming from an original picture taken into the electronic computer 35 a plurality of pictkre images different in the number of pixels, a step 2 of extracting a dark region in the picture image of a predetermined number of pixels by inspecting in the order of the picture images of less pixels the gray levels of the respective pixels in the plurality of picture images formed by the above mentioned step 1 and a step 3 of combining the region within the required gray level range near the region obtained in the above mentioned step 2 with the region obtained in the above mentioned step 2.

The above mentioned step 1 shall be explained with reference to FIGS. 9 to 11.

Figure 9:
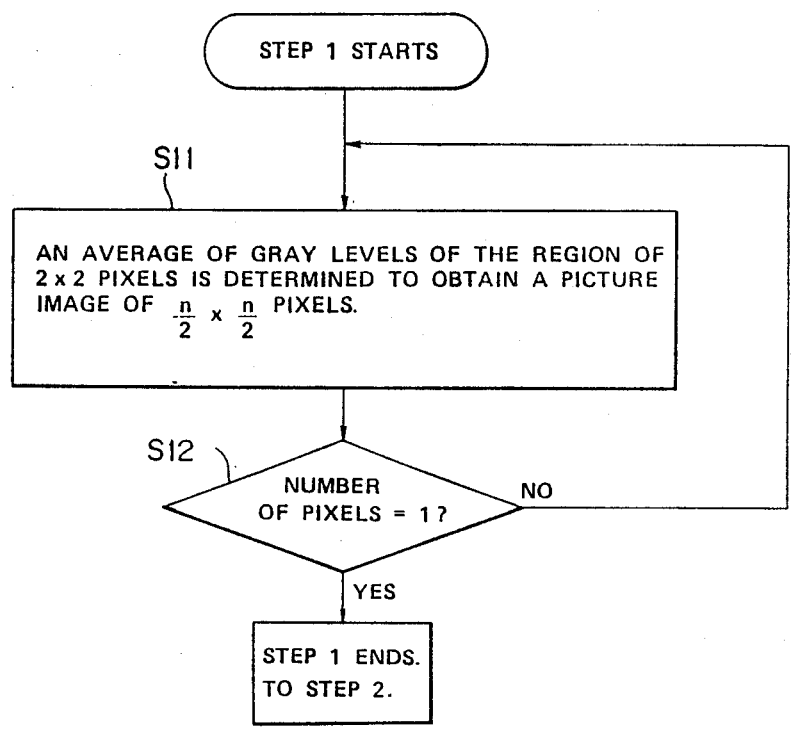

As shown in FIG. 9, in the case where the total pixels of the original picture number n×n, in step S11, an average of brightnesses (which shall be mentioned as gray levels hereinafter) of each region of 2×2 pixels is determined and a picture image of n/2×n/2 pixels is obtained. Then, in step S12, it is judged whether the number of pixels of the picture image obtained in the step S11 is 1 or not. in the case where the number of pixels is not 1, the above mentioned step S11 will be further carried out on the obtained picture image and, in the case where the number of pixels is 1, step 1 will end and the inspection will proceed to the step 2.

Thus, in step 1, picture images of less pixels are gradually formed until the number of pixels becomes 1 to make a quad-tree.

The above mentioned step 1 shall be further explained with reference to FIG. 10. By the way, in FIG. 10, xij (wherein x=a, b, c or d) represents a pixel coordinate and <xij> represents a gray level of the pixel xij.

Figure 10A:
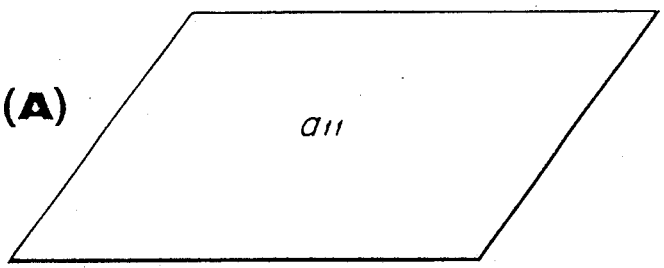
FIGS. 10(A) to 10(D) are explanatory views showing picture images of respective floors of a quad-tree.
Figure 10B:
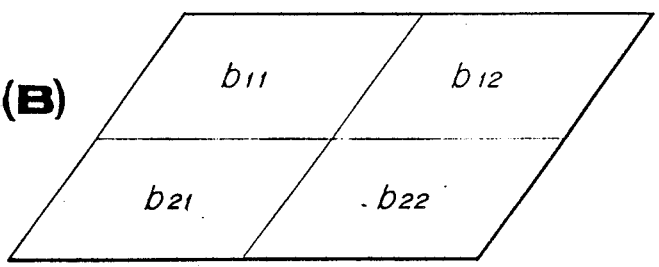
Figure 10C:
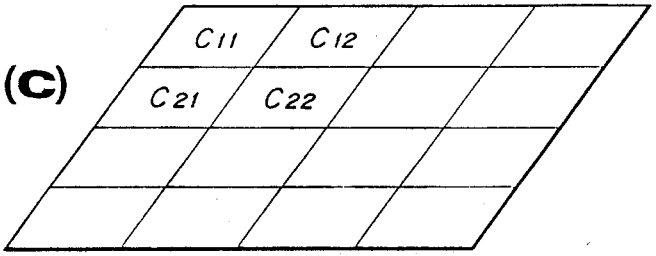
Figure 10D:
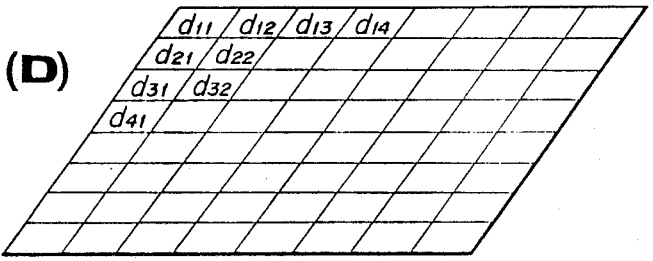

As shown in FIG. 10(D), an average of gray levels of a region of 2×2 pixels is determined by a computation of $$<c11> = \tfrac{1}{4}(<d11> + <d12> + <d21> + <d22>)$$

in a step S11 from an original picture (called a d-plane) formed of 8×8 pixels of d11, d12, --- and d88) and, as shown in FIG. 10(C), a picture image (called a c-plane) of 4×4 pixels of c11, c12, --- and c44 is obtained. In the same manner, as shown in FIG. 10(B), a picture image (called a b-plane) of 2×2 pixels of b11, b12, b21 and b 22 is obtained from $$<b11> = \tfrac{1}{4}(<c11> + <c12> + <c21> + <c22>).$$

Also, as shown in FIG. 10(A), a picture image (called an a-plane) of 1 pixel of all is obtained from $$<a11> = \tfrac{1}{4}(<b11> + <b12> + <b21> + <b22>).$$

The above operations are nothing but forming picture images of a resolution of ½ in turn.

Figure 11:
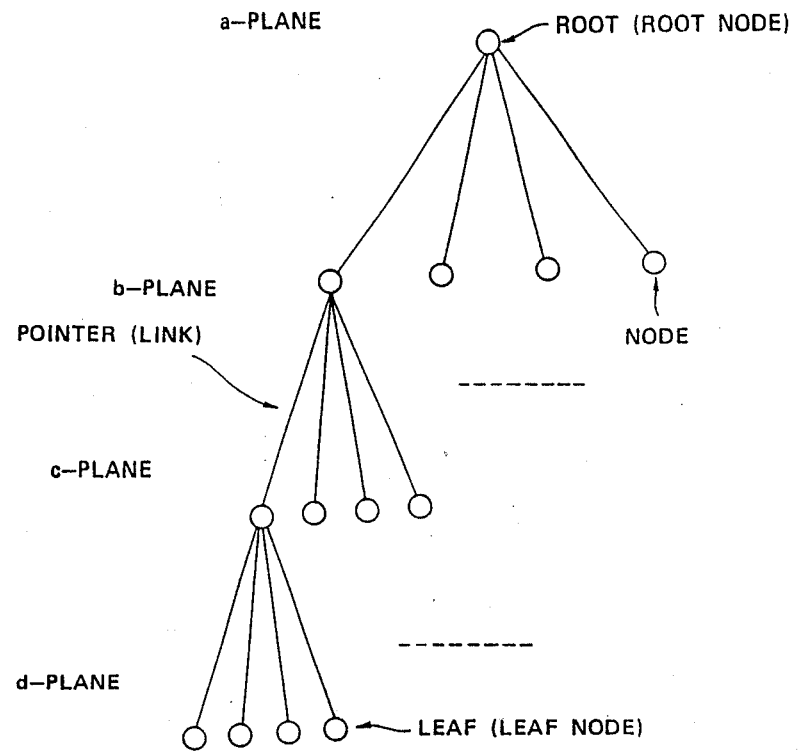
Figure 12A:
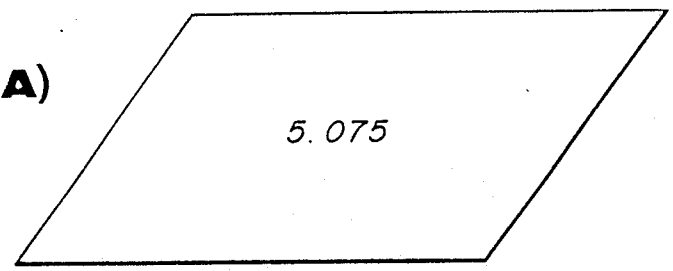
FIGS. 12(A) to 12(D) are explanatory views showing examples of picture images of the respective floors of the quad-tree to which concrete numerical values are attached.
Figure 12B:
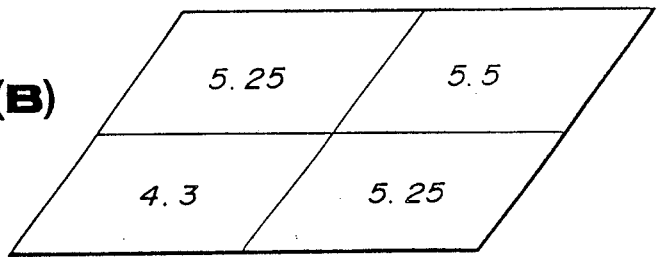
Figure 12C:
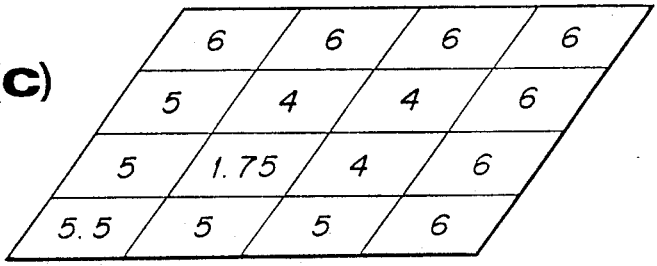
Figure 12D:
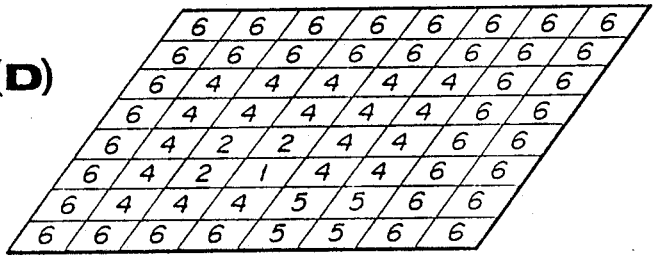

In the thus formed quad-tree, as shown in FIG. 11, the nodes of the respective planes of a, b, c and d are related through pointers or links.

Particularly, the node of the a-plane is called a root node and the node of the terminal (d-plane in this case) is called a leaf node.

Examples containing concrete numerical values of gray levels of respective pixels of respective picture images obtained by the above mentioned step 1 are shown in FIGS. 12(A) to (D).

By the way, the endoscope image displaying area is not always square but is often octagonal or circular due to the light distributing characteristics of the illuminating system. Thus, in case it is octagonal or circular, in the four corners of the picture image, there will be no endoscope image but there will be always black regions. The process is such case shall be explained on an octagonal displaying area with reference to FIGS. 13(A) to (D).

Figure 13A:
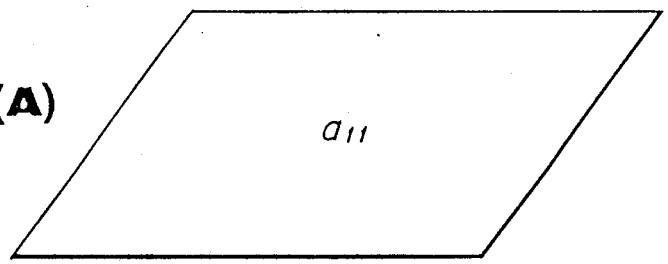
FIGS. 13(A) to 13(D) are explanatory views showing picture images of the respective floors of the quad-tree in the case where the endoscope image displaying area is octagonal.
Figure 13B:
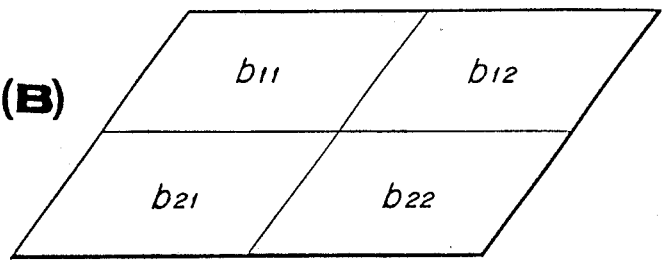
Figure 13C:
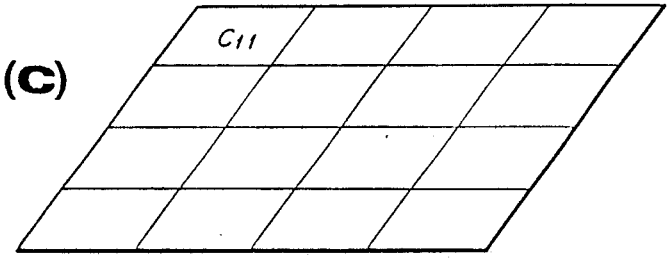
Figure 13D:
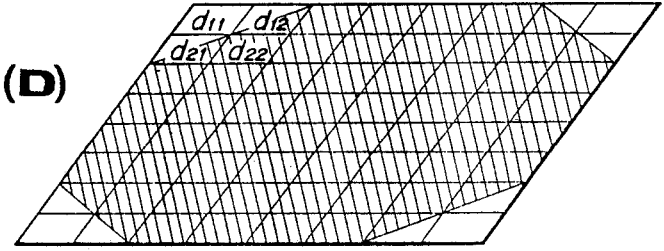

As shown in FIG. 13(D), for example, the left upper corner on the d-plane shall be explained. The entire pixel d11 and halves of the d12 and d21 are always in a black region. In such case, if <c11> is computed by $$<c11> = \tfrac{1}{4}(<d11> + <d12> + <d21> + <d22>),$$

<c11> will not show a correct value. In this case, if it is computed by $$<c11> = \tfrac{1}{4}\{2(<d12> + <d21> + <d22>)\},$$

a correct value will be obtained.

A dark region so rarely exists in the inmost corner that the pixels d11, d12 and d21 may be computed by $<c11> = \tfrac{1}{4}\{7+7+7+<d22>\}$ with the white represented by the gray level 7.

The case of the octagonal displaying area has been explained but the case of a circular or another shape can be considered to be exactly the same.

By the way, in the later explanation, in order to simplify the description, the endoscope image displaying area shall be considered to be square.

The step 2 shall be explained in the following with reference to FIGS. 14 to 17.

Figure 14:
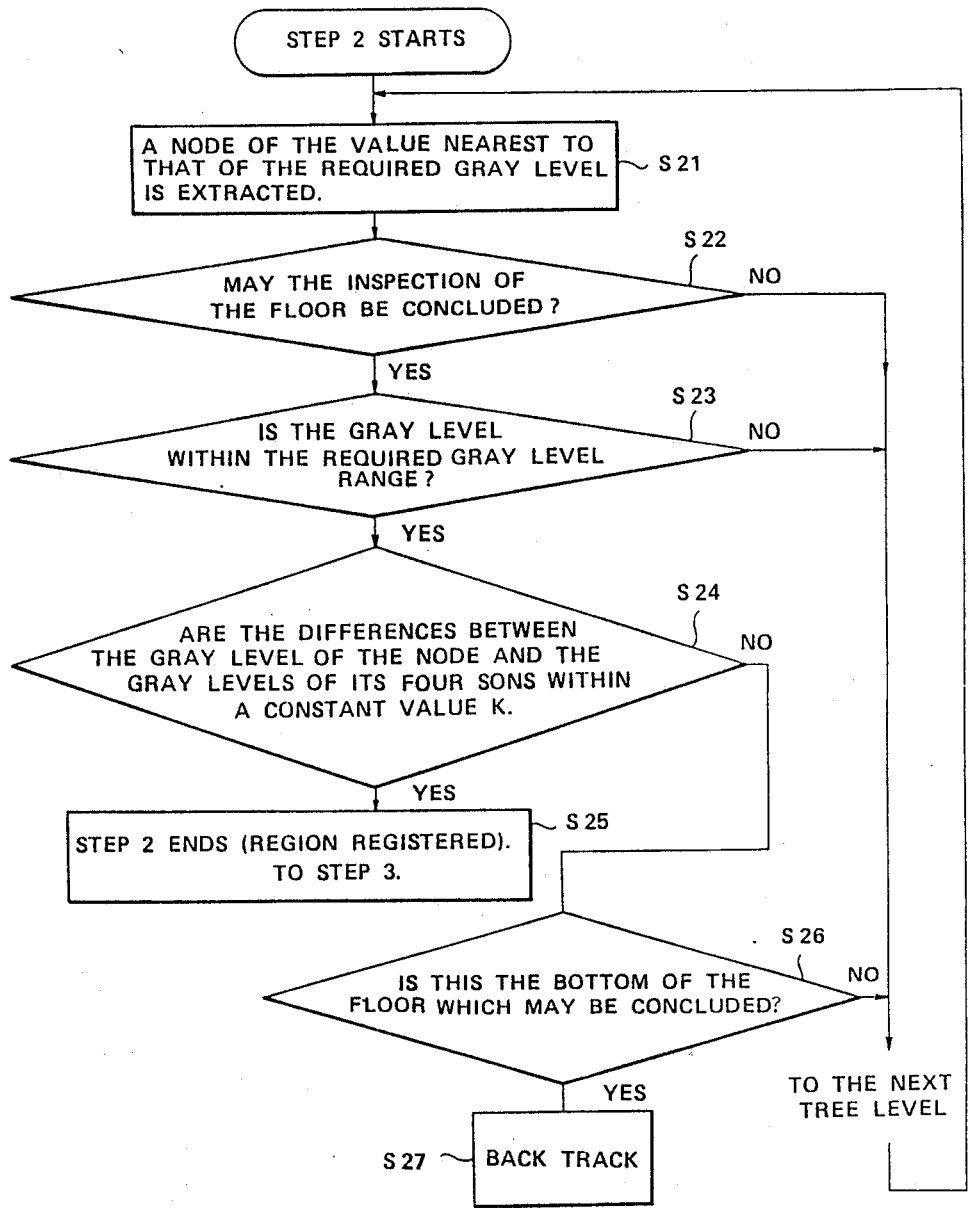

As shown in FIG. 14, first of all, in step S21, a node of the value nearest to that of the required gray level is extracted from the picture image (floor) of 2×2 pixels. Then, in step S22, it is judged whether the inspection of the floor on which the above mentioned step S21 has been made may be concluded or not. In the case where the inspection of the floor may be concluded, in step S23, it is judged whether the gray level of the node extracted in the above mentioned step S21 is in the required gray level range or not. In the case where it is in the range, in step S24, it is judged whether the differences between the gray level of the node extracted in step S21 and the gray levels of the four sons of the node are within a constant value k or not. In case they are within the constant value k, the node is registered as the required region, step 2 ends and the inspection proceeds to step 3. On the other hand, in the above mentioned step S22, in the case where it is judged that the inspection of the floor may not be concluded and, in the above mentioned step S23, in case it is judged that the gray level is not in the required gray level range, step S21 and the later steps are carried out by using the next tree level, that is, in the picture image of the next largest number of pixels (the next lower floor in the quad-tree). In such a case, in the step S21, a node of the value nearest to that of the required gray level is extracted from among the four son nodes corresponding to the node extracted by step S21 in the upper floor. Also, in the above mentioned step S24, in the case where it is judged that the gray level is not within the constant value k, in a step S26, it is judged whether the inspection has reached the lowest level of the tree to be searched or not. In this step S26, in case it is judged that the inspection may not be concluded, as described above, the step S21 and the later steps are carried out in the next tree-level. Also, in the above mentioned step S26, in case it is judged that the lowest level in the tree has been reached, in step S27, the inspection returns to the next higher floor (called a back track) and the step S21 and the later steps are carried out in the order from the node of the value nearest to that of the required gray level from among the remaining three son nodes belonging to the same parent node as the node on which, for example, the above mentioned step S21 has been already made. If all four nodes have been tried, then the inspection continues from the next higher level, and so on.

The floor of which the inspection in the above mentioned step S22 may be concluded shall be explained with reference to FIG. 15.

It is as already described that generally the number of pixels is about $512 \times 512$. The structure of the quad-tree in such a case is shown in FIG. 15. In the above mentioned step 2, the inspection is started from the floor of $2 \times 2$ pixels and is advanced downward (to the floors of more pixels) but need not always be advanced only to the floor having no problem in the precision. This reduces the processing time by an electronic computer and can eliminate the influence of noise. On the other hand, for example, the floor of $2 \times 2$ pixels is too coarse. Therefore, in the above mentioned step S22, the upper limit of the floor of which the inspection may be concluded is set in response to the required precision. In step S26, the lowest floor which is searched is selected.

The above mentioned step S24 shall be explained with reference to FIGS. 16(A) to (C).

Figure 16A:
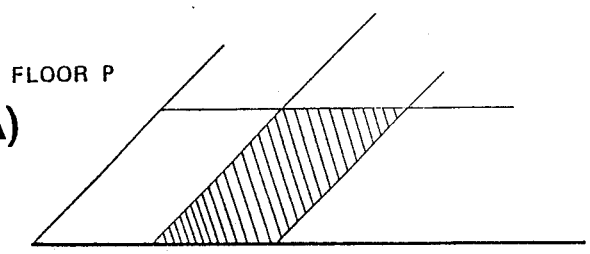
FIGS. 16(A) to 16(C) are explanatory views for explaining step S24 of the step 2.
Figure 16B:
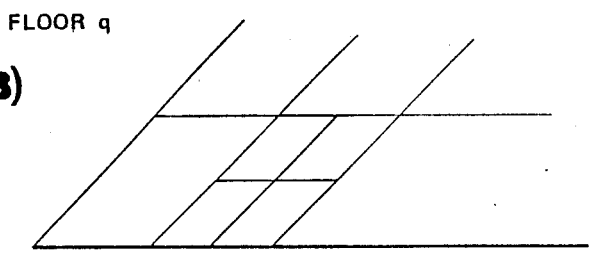
Figure 16C:
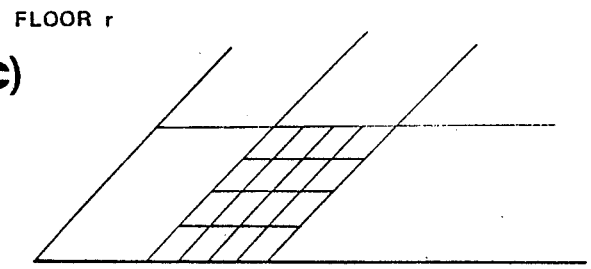
Figure 17A:
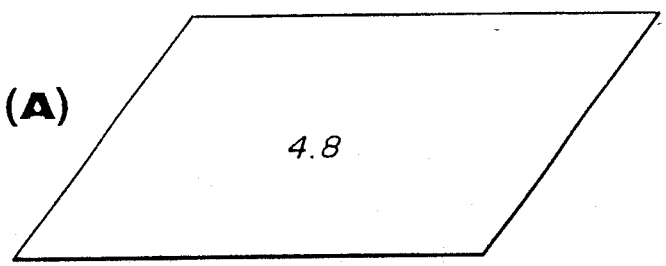
FIGS. 17(A) to 17(D) are explanatory views showing other examples of picture images of the respective floors of the quad-tree to which concrete numerical values are attached.
Figure 17B:
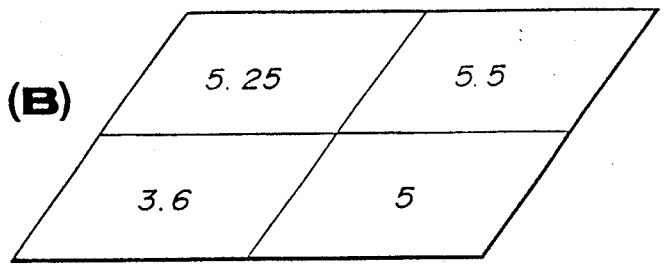
Figure 17C:
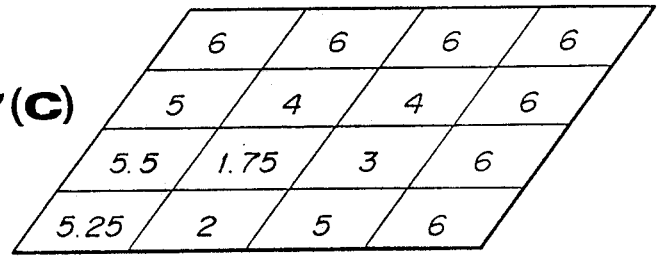
Figure 17D:
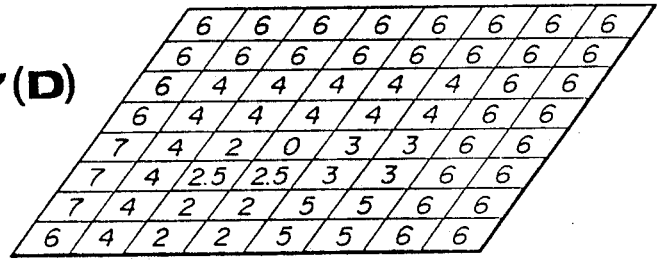

As shown in FIG. 16(A), if the differences between the gray level of the hatched part of a floor p and the gray levels of four son pixels corresponding to the above mentioned hatched part in the lower floor q are within a constant value, the brightness will be so uniform that the lower floor r need not be further inspected.

Therefore, in the above mentioned step S24, when such uniform state is found, no further inspection of the lower floor will be made. This also reduces the processing time by the electronic computer.

In the above mentioned step S24, in case it is judged that the difference of the gray levels is not within a constant value k and, in the step S26, in the case where it is judged that the inspection may be concluded, the non-uniformity of the brightness may be caused by the break of the optical fibers forming the image guide or by noise or non-uniformity in the image. In such case, the error can be prevented by back-tracking in the step S27.

Figure 19:
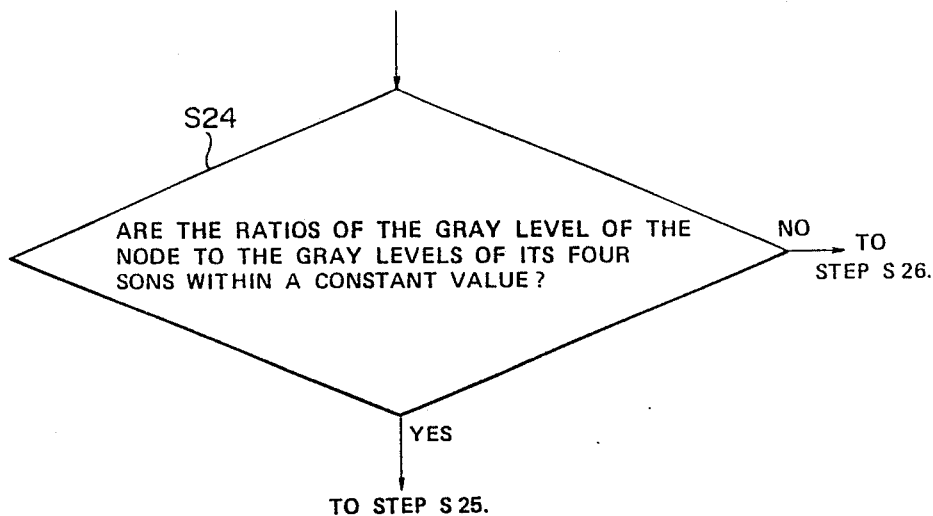
FIG. 19 is a part of a flow chart showing another example of step S24 of step 2.

By the way, in this embodiment, in the above mentioned step S24, it is judged whether the differences between the gray level of the extracted node and the respective gray levels of four son nodes of that node are within a constant value k or not. An alternate method is shown in FIG. 19. In step S24, it is judged whether the ratios of the gray levels of the respective nodes are within a constant value or not. In case the ratios are within the constant value, the step 2 may end but, in case the ratios are not within the constant value, the process may proceed to the step S26.

The operation of such step 2 as in the above shall be explained in the following by using two kinds of concrete numerical value examples.

In the first example, the gray level of the requird region shall be not more than 2. The gray level distribution shown in FIG. 12 shall be explained for example. The floor which may be concluded shall be the c-plane. The constant value k of the step S24 shall be 1.5.

First of all, in the step S21, the gray levels of four nodes on the b-plane are inspected. The node of the value nearest to that of the required gray level (not more than 2) is b21 which is extracted.

Then, in the step S22, the b-plane is judged not to be a floor which may be concluded.

Then, proceeding to the next tree-level, in the step S21, a node c32 of the value nearest to that of the required gray level is extracted from among four nodes c31, c32, c41 and c42 on the c-plane corresponding to the above mentioned node b21.

Then, in the step S22, the c-plane is judged to be a floor which may be concluded.

Then, in the step S23, the gray level of the above mentioned node c32 is judged to be in the required gray level (not more than 2).

Then, in the step S24, the gray level of the above mentioned node c32 is compared with the gray levels of d53, d54, d63 and d64 on the d-plane corresponding to this node c32. The respective gray levels of c32, d53, d54, d63 and d64 are 1 to 2 and the difference is 1 and is judged to be within a constant value k=1.5.

In the step S25, the above mentioned node c32 is registered and the step 2 ends.

In the second example, the gray level of the required region shall be not more than 2 and the gray level distributions shown in FIGS. 17(A) to (D) shall be explained for example. The floor which may be concluded shall be the c-plane. The constant value k of step S24 shall be 1.5.

First of all, in the step 21, the gray levels of four nodes on the b-plane are inspected. The node of the value nearest to that of the required gray level (not more than 2) is b21 which is extracted.

Then, in the step S22, the b-plane is judged not to be a floor which may be concluded.

Then, the inspection proceeds to the next tree-level and, in the step S21, the node c32 of the value nearest to that of the required gray level is extracted from among the four nodes of c31, c32, c41 and c42 on the c-plane corresponding to the above mentioned node b21.

Then, in the step S22, the c-plane is judged to be a floor which may be concluded.

Then, in the step S23, the gray level of the above mentioned node c32 is judged to be in the required gray level (not more than 2).

Then, in the step S24, the gray level of the above mentioned node c32 is compared with the gray levels of d53, d54, d63 and d64 on the d-plane corresponding to this node c32. The respective gray levels of c32, d53, d54, d63 and d64 are 0 to 2.5 and the difference is 2.5 and is judged not to be within a constant value k=1.5.

Then, in the step S26, it is judged whether the bottom of the floor may be concluded or not. As the bottom of the floor may be concluded, it is back-tracked in the step S27. That is to say, as the node 32 is not in the required gray level range, the same inspections in and after the step S21 are made in the order from the node of the value nearest to that of the required gray level among the other three nodes c31, c41 and c42 (in the order of c42, c41 and c31 in this case), the node c42 is extracted and is registered in the step S25 and the step 2 ends.

Step 3 shall be explained in the following paragraphs with reference to FIG. 18.

First of all, in a step S31, the gray level of the nodes adjacent to the region obtained in the above mentioned step 2 is inspected. Then, in a step S32, it is judged whether there is a region within the required gray level range or not. In the case where there is such a region, in a step S33, this region is combined with the region already obtained in the step 2 and step S31 returns. The above steps S31 to S33 are continued until there is no adjacent node within the required gray level range. On the other hand, in the above mentioned step S32, in the case that it is judged that there is no region within the required gray level range, in a step S34, it is judged whether the inspection of a higher precision is required or not and, in case it is judged not to be required, the step 3 ends. On the other hand, in the step S34, in the case where it is judged that the inspection of a higher precision is required, the inspection proceeds to the next tree-level, that is, to the lower floor and the inspection is made near the steps S31 to S33.

Now, the operation of this step 3 shall be explained, for example, with the concrete numerical values shown in FIG. 12.

In the inspection in the step 2, the node c32 is extracted and therefore, in the step 3, the inspection in the vicinity is made.

First of all, in the step S31, the gray levels of the nodes of c21, c22, c23, c31, c33, c41, c42 and c43 near the node 32 are inspected. Then, in the step S32, it is judged whether there is a region within the required gray level range (not more than 2) or not. In this example, there is no region within the required gray level range. Then, in the step S34, in case the inspection of a high precision is required, the d-plane is more minutely inspected in the steps S31 to S33. In this example, there is no region within the required gray level range.

Therefore, in this example, there is no region to be combined with the region obtained in the step 2.

Figure 20:
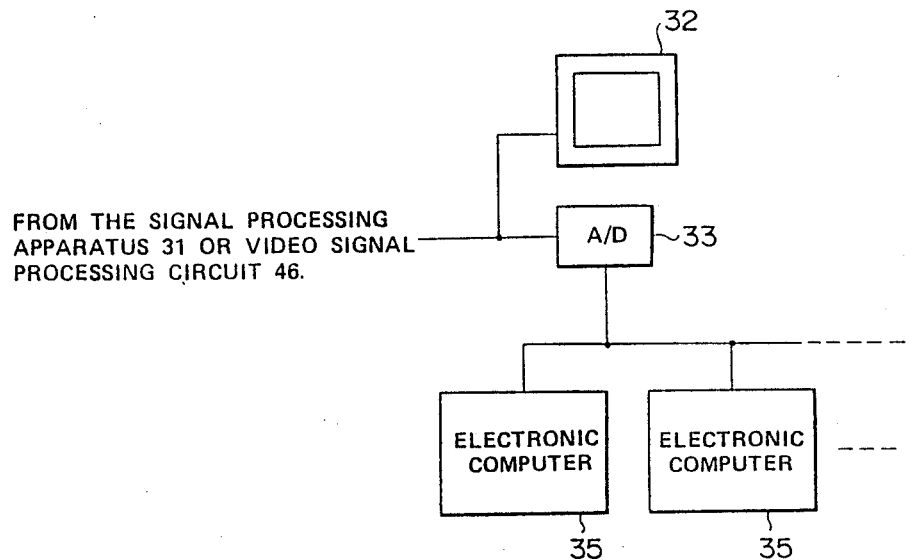
FIG. 20 is an explanatory view showing a part of an endoscope apparatus provided with a plurality of electronic computers.

By the way, as shown in FIG. 20, if a plurality of electronic computers 35 are provided and a parallel process by the plurality of electronic computers is made in the inspection in the steps 2 and 3, the processing time will be able to be reduced. It is one of the advantages of this embodiment using the quad-tree that the parallel process by the plurality of electronic computers is possible.

Thus, according to this embodiment, when the dark region extracted by the steps 1 and 2 and further combined by the step 3 in some case, an endoscope insertion direction has been found.

Now, in the case where an original picture is formed of n×n pixels, when the gray level of each of the pixels is inspected, much time will be required for the inspection. Usually, n=about 512 and n×n=262144.

On the other hand, in this embodiment, in the step 1, a quad-tree is made and, in the step 2, in extracting a dark region of a gray level of a value not larger than a predetermined value, a macro-inspection to a micro-inspection are made in the order of picture images of less pixels by using the above mentioned quad-tree. Therefore, the processing time can be remarkably reduced.

By the way, the present invention is not limited to the above mentioned embodiment. For example, the step 3 is not always required.

The endoscope may be inserted by the curving operation and inserting operation by the endoscope operator in the endoscope insertion direction detected by the method of the present invention or may be inserted by automatically directing the tip part by the apparatus in the detected inserting direction.

As explained above, according to the present invention, there is an effect that the endoscope insertion direction can be detected simply within a short processing time.

In this invention, it is apparent that working modes different in a wide range can be formed on the basis of this invention without departing from the spirit and scope of the invention. This invention is not restricted by its specific working modes except being limited by the appended claims.

What is claimed is:

1. An endoscope insertion direction detection method comprising the steps of:

forming from the same endoscope image a plurality of picture images different in the number of pixels (or picture elements) and extracting a dark region in the picture image of a predetermined number of pixels by inspecting in the order of the picture images of less pixels the gray levels of the respective pixels in the plurality of picture images formed by the said forming step, the said dark region extracted by the said extracting step being considered to be the endoscope insertion direction.

2. An endoscope insertion direction detection method according to claim 1 wherein the said endoscope image is obtained by a television camera fitted to an eyepiece part of an endoscope whereby a naked eye observation is possible.

3. An endoscope insertion direction detection method according to claim 1 wherein the said endoscope image is obtained by an imaging means provided in the endoscope.

4. An endoscope insertion direction detection method according to claim 1 wherein the said forming step includes gradually forming picture images of less pixels while reducing the number of pixels to ¼ so that, in the case where the number of pixels is reduced to ¼, the gray level of one pixel in the picture image of less pixels will be of an average value of the gray levels of four son pixels of 2×2 in the picture image of more pixels corresponding to the said one pixel.

5. An endoscope insertion direction detection method according to claim 4 wherein the said extracting step includes inspecting the gray levels of the respective pixels in a picture image, extracting the pixel nearest to a required gray level, then inspecting the gray levels of four son pixels of the extracted pixel and extracting the pixel nearest to the required gray level.

6. An endoscope insertion direction detection method according to claim 4 wherein the said extracting step includes parallel processing by using a plurality of electronic computers.

7. An endoscope insertion direction detection method according to claim 4 wherein the said extracting step includes ending the inspection when the differences of the gray levels of the said four son pixels to the father become not larger than a predetermined value.

8. An endoscope insertion direction detection method according to claim 4 wherein the said extracting step includes ending the inspection when the ratios of the gray levels of the said four son pixels to the father become not larger than a predetermined value.

9. An endoscope insertion direction detection method according to claim 4 wherein the said forming step includes forming a plurality of picture images by considering pixels to be white in a black region outside an endoscope image.

10. An endoscope insertion direction detection method according to claim 4 wherein the said forming step includes forming a plurality of picture images by removing the black region outside an endoscope image.

11. An endoscope insertion direction detection method according to claim 4 wherein the said extracting step includes setting the upper limit and lower limit of the floor of which the inspection may be concluded in response to a required precision.

12. An endoscope insertion direction detection method according to claim 4 comprising a further step of extracting a region within a predetermined gray level range near the said dark region extracted by the said extracting step and combining the said region with the said dark region extracted by the said extracting step.

13. An endoscope insertion direction detection method according to claim 4 wherein the gray level of the said pixel is in a digital amount in the said forming step and extracting step.

14. An endoscope insertion direction detection method comprising a step of extracting a dark region in an endoscope image, said dark region extracted by the said step being considered to be the endoscope inserting direction.

* * * * *